US012672836B2

(12) United States Patent
Kopel et al.

(10) Patent No.: US 12,672,836 B2
(45) Date of Patent: Jul. 7, 2026

(54) HANDLING RESPIRATION DURING NAVIGATIONAL BRONCHOSCOPY

(71) Applicant: Covidien LP, Mansfield, MA (US)

(72) Inventors: Evgeni Kopel, Barkan (IL); John W. Komp, Dillon, CO (US); Scott E.M. Frushour, Boulder, CO (US); Scott Robert Tiesma, Brooklyn Park, MN (US); William J. Dickhans, Longmont, CO (US); Christopher Michael Kolin, Mapel Grove, MN (US)

(73) Assignee: Covidien LP, Mansfield, MA (US)

( * ) Notice: Subject to any disclaimer, the term of this patent is extended or adjusted under 35 U.S.C. 154(b) by 994 days.

(21) Appl. No.: 17/870,532

(22) Filed: Jul. 21, 2022

(65) Prior Publication Data

US 2024/0023917 A1 Jan. 25, 2024

(51) Int. Cl.
A61B 6/46 (2024.01)
A61B 6/12 (2006.01)
(Continued)

(52) U.S. Cl.
CPC .............. A61B 6/463 (2013.01); A61B 6/12 (2013.01); A61B 6/4057 (2013.01); A61B 6/465 (2013.01);
(Continued)

(58) Field of Classification Search
CPC ......... A61B 6/463; A61B 6/12; A61B 6/4057; A61B 6/465; A61B 17/12036; A61B 17/12104; A61B 17/12136; A61B 34/25; A61B 2034/105; A61B 2090/3945; A61B 2090/3966; A61B 34/20; A61B 2017/00699; A61B 2017/00809; A61B 2034/2048; A61B 2034/2051; A61B 2034/2061; A61B 2034/2063; A61B 2090/376
See application file for complete search history.

(56) References Cited

U.S. PATENT DOCUMENTS 5,480,422 A 1/1996 Ben-Haim
5,558,091 A 9/1996 Acker et al.
(Continued)

FOREIGN PATENT DOCUMENTS

WO 2006095221 A2 9/2006

OTHER PUBLICATIONS

Extended European Search Report issued in European Patent Application No. 23186803.5 dated Dec. 14, 2023.

*Primary Examiner* — Navin Natnithithadha
(74) *Attorney, Agent, or Firm* — Weber Rosselli & Cannon LLP

(57) ABSTRACT

Methods of respiration compensation including detecting a position of a catheter proximate a target within a patient, performing a local registration to update a displayed relative position and orientation of the catheter and the target in a three-dimensional model, detecting movement of a plurality of sensors, determining a respiration waveform from the detected movement of the plurality of sensors, and indicating on a user-interface a period during which advancement of a biopsy or therapy tool from the catheter is most likely to intersect the target, wherein the period corresponds to a portion of the respiration waveform during which the movement of the plurality of sensors is within a desired range.

20 Claims, 5 Drawing Sheets

(51) Int. Cl.
    *A61B 6/40*         (2024.01)
    *A61B 17/12*      (2006.01)

(52) U.S. Cl.
    CPC .. *A61B 17/12036* (2013.01); *A61B 17/12104*
             (2013.01); *A61B 17/12136* (2013.01)

(56)         References Cited

U.S. PATENT DOCUMENTS

| | | | |
|---|---|---|---|
| 5,729,129 | A | 3/1998 | Acker |
| 5,752,513 | A | 5/1998 | Acker et al. |
| 5,928,248 | A | 7/1999 | Acker |
| 6,016,439 | A | 1/2000 | Acker |
| 6,147,480 | A | 11/2000 | Osadchy et al. |
| 6,161,032 | A | 12/2000 | Acker |
| 6,201,387 | B1 | 3/2001 | Govari |
| 6,203,493 | B1 | 3/2001 | Ben-Haim |
| 6,211,666 | B1 | 4/2001 | Acker |
| 6,233,476 | B1 | 5/2001 | Strommer et al. |
| 6,314,310 | B1 | 11/2001 | Ben-Haim et al. |
| 6,332,089 | B1 | 12/2001 | Acker et al. |
| 6,335,617 | B1 | 1/2002 | Osadchy et al. |
| 6,366,799 | B1 | 4/2002 | Acker et al. |
| 6,373,240 | B1 | 4/2002 | Govari |
| 6,427,314 | B1 | 8/2002 | Acker |
| 6,453,190 | B1 | 9/2002 | Acker et al. |
| 6,484,118 | B1 | 11/2002 | Govari |
| 6,580,938 | B1 | 6/2003 | Acker |
| 6,591,129 | B1 | 7/2003 | Ben-Haim et al. |
| 6,618,612 | B1 | 9/2003 | Acker et al. |
| 6,650,927 | B1 | 11/2003 | Keidar |
| 6,690,963 | B2 | 2/2004 | Ben-Haim et al. |
| 6,788,967 | B2 | 9/2004 | Ben-Haim et al. |
| 6,995,729 | B2 | 2/2006 | Govari et al. |
| 7,197,354 | B2 | 3/2007 | Sobe |
| 7,236,567 | B2 | 6/2007 | Sandkamp et al. |
| 7,286,868 | B2 | 10/2007 | Govari |
| 7,301,332 | B2 | 11/2007 | Govari et al. |
| 7,321,228 | B2 | 1/2008 | Govari |
| 7,324,915 | B2 | 1/2008 | Altmann et al. |
| 7,343,195 | B2 | 3/2008 | Strommer et al. |
| 7,353,125 | B2 | 4/2008 | Nieminen et al. |
| 7,366,562 | B2 | 4/2008 | Dukesherer et al. |
| 7,370,656 | B2 | 5/2008 | Gleich et al. |
| 7,373,271 | B1 | 5/2008 | Schneider |
| 7,386,339 | B2 | 6/2008 | Strommer et al. |
| 7,397,364 | B2 | 7/2008 | Govari |
| 10,231,788 | B2 * | 3/2019 | Olson ............... A61M 25/0147 |
| 10,881,466 | B2 | 1/2021 | Krimsky et al. |
| 11,701,492 | B2 * | 7/2023 | Komp ................... A61B 34/25 |
| | | | 600/424 |
| 12,208,220 | B2 * | 1/2025 | Komp ................... A61B 34/25 |
| 2001/0031919 | A1 | 10/2001 | Strommer et al. |
| 2003/0086599 | A1 | 5/2003 | Armato et al. |
| 2003/0185346 | A1 | 10/2003 | Vilsmeier |
| 2004/0086161 | A1 | 5/2004 | Sivaramakrishna et al. |
| 2004/0097804 | A1 | 5/2004 | Sobe |
| 2004/0097805 | A1 | 5/2004 | Verard et al. |
| 2004/0138548 | A1 | 7/2004 | Strommer et al. |
| 2004/0249267 | A1 | 12/2004 | Gilboa |
| 2005/0033149 | A1 | 2/2005 | Strommer et al. |
| 2005/0107688 | A1 | 5/2005 | Strommer |
| 2005/0197566 | A1 | 9/2005 | Strommer et al. |
| 2006/0058647 | A1 | 3/2006 | Strommer et al. |
| 2006/0064006 | A1 | 3/2006 | Strommer et al. |
| 2006/0074292 | A1 | 4/2006 | Thomson et al. |
| 2006/0149134 | A1 | 7/2006 | Soper et al. |
| 2007/0167738 | A1 | 7/2007 | Timinger et al. |
| 2007/0167743 | A1 | 7/2007 | Honda et al. |
| 2007/0167806 | A1 | 7/2007 | Wood et al. |
| 2007/0287901 | A1 | 12/2007 | Strommer et al. |
| 2008/0097187 | A1 | 4/2008 | Gielen et al. |
| 2008/0132909 | A1 | 6/2008 | Jascob et al. |
| 2008/0132911 | A1 | 6/2008 | Sobe |
| 2008/0139915 | A1 | 6/2008 | Dolan et al. |
| 2008/0157755 | A1 | 7/2008 | Kruger et al. |
| 2008/0161682 | A1 | 7/2008 | Kendrick et al. |
| 2008/0162074 | A1 | 7/2008 | Schneider |
| 2008/0183071 | A1 | 7/2008 | Strommer et al. |
| 2008/0188749 | A1 | 8/2008 | Rasche et al. |
| 2009/0080737 | A1 | 3/2009 | Battle et al. |
| 2009/0281566 | A1 | 11/2009 | Edwards et al. |
| 2013/0096572 | A1 * | 4/2013 | Donhowe ............. A61B 34/10 |
| | | | 606/130 |
| 2014/0238398 | A1 * | 8/2014 | Christopher ........... A61B 5/087 |
| | | | 128/204.22 |
| 2018/0279852 | A1 * | 10/2018 | Rafii-Tari ............... G16H 40/63 |
| 2019/0005687 | A1 * | 1/2019 | Weingarten ........... G06T 19/003 |
| 2020/0246079 | A1 * | 8/2020 | Shevlev ................. A61B 34/20 |
| 2021/0030482 | A1 | 2/2021 | Alexandroni et al. |
| 2021/0169583 | A1 * | 6/2021 | Gleiman ............... A61B 5/065 |
| 2021/0378759 | A1 | 12/2021 | Komp et al. |
| 2021/0379332 | A1 * | 12/2021 | Komp ............... A61B 1/00006 |
| 2022/0022840 | A1 * | 1/2022 | Birenbaum ............. A61B 6/12 |
| 2023/0310805 | A1 * | 10/2023 | Komp ............... A61B 1/00006 |
| | | | 600/424 |
| 2023/0363832 | A1 * | 11/2023 | Mosadegh ............. G16H 20/40 |
| 2025/0121160 | A1 * | 4/2025 | Komp ..................... A61B 6/12 |

* cited by examiner

200

400

HANDLING RESPIRATION DURING NAVIGATIONAL BRONCHOSCOPY

FIELD

This disclosure relates to methods and systems to combat the effects of respiration and heartbeat in intraprocedural imaging, diagnostic, and therapeutic procedures.

BACKGROUND

A fluoroscopic imaging device is commonly located in the operating room during navigation procedures. The standard fluoroscopic imaging device may be used by a clinician, for example, to visualize and confirm the placement of a medical device after it has been navigated to a desired location. However, although standard fluoroscopic images display highly dense objects such as metal tools and bones as well as large soft-tissue objects such as the heart, the fluoroscopic images have difficulty resolving small soft-tissue objects of interest such as lesions. Furthermore, the fluoroscope image is only a two-dimensional (2D) projection. Thus, volumetric imaging is needed to navigate within the body safely and accurately. However, even volumetric imaging cannot on its own eliminate imprecision caused by respiration of the patient.

SUMMARY

This disclosure generally relates to systems and methods for reducing the impact of respiration on navigation of a catheter to a target to improve biopsy yields and therapy outcomes.

One aspect of the disclosure is directed to a method of respiration compensation, the method includes detecting a position of a catheter proximate a target within a patient. The method of respiration compensation also includes performing a local registration to update a displayed relative position and orientation of the catheter and the target in a three-dimensional model; detecting movement of a plurality of sensors; determining a respiration waveform from the movement of the plurality of sensors; and indicating on a user-interface a period during which advancement of a biopsy or therapy tool from the catheter is most likely to intersect the target, where the period corresponds to a portion of the respiration waveform during which the movement of the plurality of sensors is within a desired range. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method where the period is during an expiration phase of the respiratory waveform. The method further including displaying the respiration waveform on the user-interface. The method where performing the local registration further includes detecting the achievement of a breath hold of the patient. The method where breath hold is achieved following cessation of ventilation of the patient and an off-set period to allow for expansion of lungs of the patient. The method where the ventilation waveform is configured to achieve a desired respiration waveform. The method where an off-set period is calculated based on comparison of the ventilation waveform and the respiration waveform. The method where performing the local registration further includes receiving fluoroscopic images and identifying those images acquired during a desired portion of the respiration waveform. The method further including determining angles at which additional images are required to complete a fluoroscopic sweep. The method further including orienting the fluoroscope to the determined angles and collecting additional images during a desired portion of the respiration waveform to complete the fluoroscopic sweep. The orienting of the fluoroscope is performed automatically. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

A further aspect of the disclosure is directed to a method of respiration compensation including detecting movement of a plurality of sensors, determining a respiration waveform the movement of the plurality of sensors, detecting a position of a catheter proximate a target within a patient. The method of respiration compensation also includes acquiring a plurality of fluoroscopic images with a fluoroscope, where the fluoroscopic images include a distal portion of the catheter and the target; identifying individual images of the plurality of fluoroscopic images acquired during a desired portion of the respiration waveform; determining angles at which additional images are required to complete a fluoroscopic sweep; orienting the fluoroscope to the determined angles and collecting additional images during a desired portion of the respiration waveform to complete the fluoroscopic sweep; performing a local registration, by identifying the catheter and the target in two or more images from the fluoroscopic sweep; updating a displayed relative position and orientation of the catheter and the target in a 3d model; and indicating on a user-interface a period during which advancement of a biopsy or therapy tool from the catheter is most likely to intersect the target, where the period corresponds to the desired portion of the respiration waveform. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method where the desired portion of the respiration waveform is a portion with the slowest rate of change of position of the plurality of sensors. The desired portion of the respiration waveform is a part of an expiration phase. The method further including receiving a ventilation waveform from a ventilator supplying air to the patient. The ventilation waveform is configured to minimize movement of the plurality of sensors and achieve a desire state of inflation of lungs of the patient. The method where a balloon inflated and configured to reduce blood and airflow distal of the balloon in the lungs of the patient. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Still a further aspect of the disclosure is directed to a method of respiration compensation that includes detecting movement of a plurality of sensors on an exterior of a patient, determining a respiration waveform the movement of the plurality of sensors, detecting a position of a catheter proximate a target within the patient, receiving a ventilation waveform from a ventilator supplying air to the patient. The method of respiration compensation also includes receiving data from an airflow sensor configured on a distal portion of the catheter and determine a state of atelectasis of a portion of a lung proximate the distal portion of the catheter; and indicating on a user-interface a period during which advancement of a biopsy or therapy tool from the catheter is most likely to intersect the target, where the period corresponds to a portion of the respiration waveform during which the movement of the plurality of sensors is within a desired range. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method further including performing a local registration to update a relative position and orientation of the catheter and target in a three-dimensional model. The local registration is achieved by: acquiring a plurality of fluoroscopic images with a fluoroscope, where the fluoroscopic images include a distal portion of the catheter and the target; identifying individual images of the plurality of fluoroscopic images acquired during a desired portion of the respiration waveform; determining angles at which additional images are required to complete a fluoroscopic sweep; orienting the fluoroscope to the determined angles and collecting additional images during the desired portion of the respiration waveform to complete the fluoroscopic sweep; and identifying the catheter and the target in two or more images from the fluoroscopic sweep. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Various exemplary aspects are illustrated in the accompanying figures. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. The figures are listed below.

DETAILED DESCRIPTION

Figure 1:
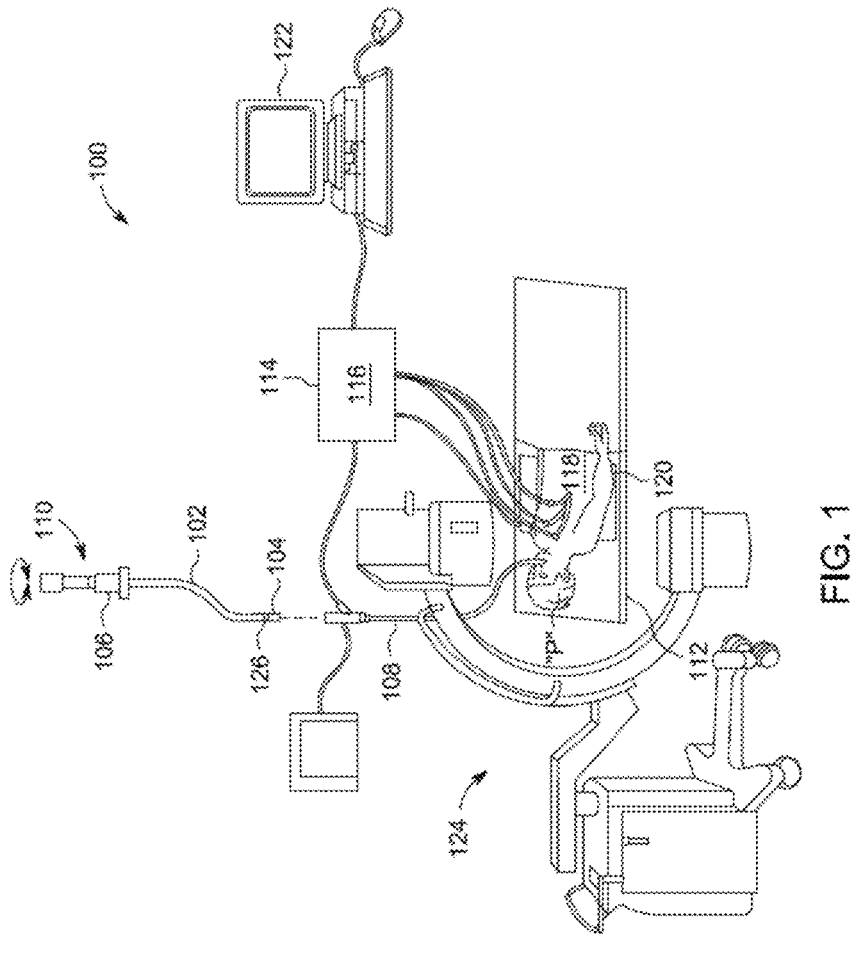
FIG. 1 is a schematic diagram of a systems for lung navigation and imaging in accordance with the disclosure.

There are a variety of known systems and methods whereby pre-procedural images are acquired and analyzed prior to engaging in diagnostic and therapeutic procedures. One such system is the ILLUMISITE™ system offered by MEDTRONIC. In use, these systems generally require the acquisition of computed tomography (CT) images of the relevant portion of the anatomy (e.g., the lungs), though as will be recognized other imaging modalities such as magnetic resonance images (MRI), fluoroscopic images, cone beam CT images (CBCT), positron emission tomography (PET) images and others may be employed for the pre-procedural image acquisition. Following acquisition of the pre-procedural images, a three-dimensional (3D) model of the portion of the anatomy may be constructed and the acquired images can be reviewed to determine the presence of and the locations of target tissue (e.g., potential tumors or lesions requiring biopsy or therapy). Following determination of the presence and location of target tissue, a pathway through the body to the target tissue is constructed.

The 3D model and the determined pathway through the anatomy can then be employed in an actual procedure. For example, by using a sensor system (e.g., electromagnetic (EM) sensor, shape sensor, ultrasound sensor, or others) a clinician can advance a catheter or other tool following the pathway to reach the target tissue. This advancement may be manual, motor guided with clinician input, or fully robotic without departing from the scope of the disclosure. As will be appreciated some form of registration, relating the coordinate system of the pre-procedural imaging to the actual positions of the anatomy of the patient. Once registered, the sensed location of the catheter or tool in the anatomy of the patient is depicted in the 3D model. As the catheter or tool is advanced the displayed position is constantly updated to provide an indication to the clinician of proximity to the target tissue so that diagnostic or therapeutic procedures can be undertaken of the target tissue.

While in concept this is a straightforward process, the reality is more complex. As an initial matter, at least with respect to the lungs, the pre-procedural images are often taken at so called full breath hold. This means that the patient is asked to fill their lungs with air, which as will be appreciated is not the typical state of the lungs of a patient, both during normal breathing and when undergoing a medical procedure. Secondly, the images are often acquired days and even weeks before the actual procedure. Thus, the position of the patient during the procedure is necessarily very different from the one the patient is in during the imaging, as are the positions of organs internal to the patient. The result is a divergence between the position of tissue, such as the target tissue, and the position of patient's actual anatomy. This is referred to as CT-to-body-divergence, which as can be appreciated can result in the imprecise navigation of the catheter or tool to the target tissue.

To combat CT-to-body divergence, systems and methods for acquiring and analyzing intraprocedural images have been designed and implemented. In one such intraprocedural imaging process, FLUORONAV as implemented in ILLUMISITE™, a fluoroscopic sweep is undertaken of the patient following navigation of the catheter or tool proximate the target tissue. The position of the catheter or tool is identified in one or more of the fluoroscopic images. Additionally, the position of the target tissue is also identified in at least one fluoroscopic image. With the catheter or tool and the lesion identified in these images, the relative positions and orientation of the catheter or tool and the target tissue in the patient is determined. The relative positions, as determined in the fluoroscopic images, is used to update the display of the relative positions of the catheter or tool and the target tissue in the 3D model. This local registration helps to alleviate the effects of CT-to-body divergence and allows for confidence in the so called "last mile" of navigation (e.g., the final 3 cm or less) to perform the diagnostic or therapeutic procedure.

However, even with intraprocedural imaging to combat CT-to-body divergence there remains a consistent and repeated necessary function of life that can result in imprecision in that last mile of navigation or even in acquiring the intraprocedural images. Specifically, the instant disclosure is directed to providing methods and systems to combat the effects of respiration and heartbeat in intraprocedural imaging, diagnostic, and therapeutic procedures.

FIG. 1 is a perspective view of an exemplary system for navigation of a medical device, e.g., a biopsy or treatment tool, to a target via airways of the lungs. One aspect of the system 100 is a software application for reviewing computed tomography (CT) image data that has been acquired separately from system 100. The review of the CT image data allows a user to identify one or more targets and plan a pathway to an identified target. This is typically referred to as a planning phase. The planning may be done manually, automatically, or combinations of the two, where for example a proposed plan is presented to the clinician for review and acceptance, rejection, or modification. Another aspect of the software application is a navigation phase which allows a user to navigate a catheter or other tool to a target (navigation phase) using a user interface and confirm placement of the catheter or a tool relative to the target. The target is typically tissue of interest for biopsy or treatment that was identified during the planning phase by review of the CT image data. Following navigation, a medical device, such as a biopsy tool or treatment tool, may be inserted into the catheter to obtain a tissue sample from the tissue located at, or proximate to, the target or to treat such tissue. The treatment tool may be selected to achieve microwave ablation, radio-frequency ablation, cryogenic ablation, chemical ablation, or other treatment mechanism of the target as preferred by the clinician.

One aspect of FIG. 1 is a catheter guide assembly 102 including a sensor 104 at a distal end. The catheter guide assembly 102 includes a catheter 106. In one aspect, catheter 106 is inserted into a bronchoscope 108 for access to a luminal network of the patient P. Specifically, catheter 106 of catheter guide assembly 102 may be inserted into a working channel of bronchoscope 108 for navigation through a patient's luminal network. However, as noted elsewhere herein, the catheter guide assembly 102 may itself be articulatable and navigable without requiring the use of a bronchoscope 108. If the system 100 is configured for electromagnetic navigation (EMN), a locatable guide (LG) 110, which may include the sensor 104 such as an electromagnetic (EM) sensor may be inserted into catheter 106 and locked into position such that sensor 104 extends a desired distance beyond the distal tip of catheter 106. However, it should be noted that the sensor 104 may be incorporated into one or more of the bronchoscope 108, catheter 106, or a biopsy or treatment tool, without departing from the scope of the disclosure. In one embodiment, in addition to sensor 104, as second sensor 126 is incorporated into the catheter 106 and provides position information of the distal portion of the catheter 106 following removal of the LG 110 from the catheter 106.

The catheter 106 may be inserted into the bronchoscope 108, and the distal end of the catheter 106 and LG 110 both extend beyond the distal end of the bronchoscope 108. Those of skill in the art will recognize that the catheter 106 may be navigated within the patient without employing the use of the bronchoscope 108, without departing from the scope of the disclosure. The position or location and orientation of sensor 104 and thus the distal portion of LG 110, within an electromagnetic field can be derived based on location data in the form of currents produced by the presence of the EM sensors in a magnetic field, or by other means described herein. In some aspects, the methods of the disclosure may include visualizing and/or displaying the status information of the LG 110. Though the use of EM sensors and EMN are not required as part of this disclosure, their use may further augment the utility of the disclosure in endoluminal navigation (e.g., navigation of the lungs). As the bronchoscope 108, catheter 106, LG 110 or other tool could be used interchangeably or in combination herein, the term catheter will be used here to refer to one or more of these elements. Further, as an alternative to the use of EM sensors, flex sensors such as fiber Bragg sensors, ultrasound sensors, accelerometers, and others may be used in conjunction with this disclosure to provide outputs to the tracking system 114 for determination of the position of a catheter including without limitation the bronchoscope 108, catheter 106, LG 110, or biopsy or treatment tools, without departing from the scope of this disclosure.

System 100 may generally include an operating table 112 configured to support a patient P, a bronchoscope 108 configured for insertion through patient P's mouth into patient P's airways. Though not shown, those of skill in the art will recognize that the bronchoscope 108 may be inserted into the patient through an intubation tube. System 100 may further include a monitor 114 coupled to bronchoscope 108 (e.g., a video display, for displaying the video images received from the video imaging system of bronchoscope 108). If configured for EMN, system 100 may include a locating or tracking system 116, a plurality of reference EM sensors 118 and a transmitter mat 120 including a plurality of radio-opaque or partially radio-opaque markers 121 that can be detected in fluoroscopic images of the patient.

Also included is a computing device 122 including software and/or hardware used to facilitate identification of a target, pathway planning to the target, navigation of a medical device to the target, and/or confirmation and/or determination of placement of catheter 106, or a suitable device therethrough, relative to the target. Computing device 122 may be similar to workstation 1001 of FIG. 5 and may be configured to execute the methods of the disclosure. Computing device 122 may be any suitable computing device including a processor and storage medium, wherein the processor is capable of executing instructions stored on the storage medium as one or more applications. Computing device 122 may further include a database configured to store patient data, CT data sets including CT images, fluoroscopic data sets including fluoroscopic images and video, fluoroscopic 3D reconstruction, navigation plans, and any other such data. Although not explicitly illustrated, computing device 122 may include inputs, or may otherwise be configured to receive, CT data sets, fluoroscopic images/ video and other data described herein. Additionally, computing device 122 includes a display configured to display graphical user interfaces. Computing device 122 may be connected to one or more networks through which one or more databases may be accessed. Further details of the computing device are described in connection with FIG. 5, below.

With respect to the planning phase, computing device 122 utilizes previously acquired CT image data for generating and viewing a 3D model or rendering of patient P's airways, enables the identification of a target on the 3D model (automatically, semi-automatically, or manually), and allows for determining a pathway through patient P's airways to tissue located at and around the target. More specifically, CT images and CT image data sets acquired from CT scans are processed and assembled into a 3D CT volume, which is then utilized to generate a 3D model of patient P's airways. The 3D model may be displayed on a display associated with computing device 122, or in any other suitable fashion. An example of such a user interface can be seen in FIG. 11. Using computing device 122, various views of the 3D model or enhanced two dimensional images generated from the 3D model are presented. The enhanced two-dimensional images may possess some 3D capabilities because they are generated from 3D data. The 3D model may be manipulated to facilitate identification of target on the 3D model or two-dimensional (2D) images, and selection of a suitable pathway through patient P's airways to access tissue located at the target can be made. Once selected, the pathway plan, three-dimensional model, and images derived therefrom, can be saved and exported to a navigation system for use during the navigation phase(s).

A fluoroscopic imaging device 124 capable of acquiring fluoroscopic or x-ray images or video of the patient P (which may be referred to generally as fluoroscopic image data sets) is also included in system 100. As shown in FIG. 1, the fluoroscopic imaging device 124 is in the form of a C-arm fluoroscope, which moves relative to the patient P so that fluoroscopic images may be acquired from different angles or perspectives relative to patient P to generate a sequence of fluoroscopic images, such as a fluoroscopic video. The fluoroscopic images, sequence of fluoroscopic images, or video captured by fluoroscopic imaging device 124 may be stored within fluoroscopic imaging device 124 or transmitted to computing device 122 for storage, processing, and display. Additionally, fluoroscopic imaging device 124 may. The pose of fluoroscopic imaging device 124 relative to patient P and while capturing the fluoroscopic images may, in one aspect of the disclosure, be estimated using the markers incorporated on or in the transmitter matt 120 and pose estimation and image processing techniques described hereinbelow.

The markers may be incorporated into the transmitter mat 120, incorporated into the operating table 112, or otherwise incorporated into another appliance placed on or near the operating table 112 so that they can be seen in the fluoroscopic images. The markers are generally positioned under patient P and between patient P and a radiation source or a sensing unit of fluoroscopic imaging device 124. Fluoroscopic imaging device 124 may include a single imaging device or more than one imaging device.

As will be appreciated by one of ordinary skill in the art, other methods of determining the pose of a fluoroscope 124 may also be employed without departing from the scope of the disclosure. For example, BLUETOOTH® enabled or wired devices mounted on the fluoroscope 124 can output an indication of its rotational pose. Additionally or alternatively, the fluoroscope 124 itself may track and output an indication of its pose during the capture of the fluoroscopic images.

One aspect of the disclosure involves utilizing the output of the reference sensors 118. The reference sensors 118 are placed on the chest of the patient and their movement within the EM field generated by the transmitter mat 120 can be detected. Placement of three reference sensors 118 provide for different measurements of movement of the patient's chest as they breath. In addition, due to the sensitivity of the reference sensors 118 movements caused by the heartbeat of the patient, which are smaller in amplitude but occurring at a distinct and much higher frequency can also be detected.

In accordance with this aspect of the disclosure, the waveform of the respiration can be detected based on the movement of the reference sensors 118 in the EM field generated by the transmitter mat 120. An example of this aspect is described in connection with the method 200 of FIG. 2. In accordance with the method, and consistent with the procedures described herein above, the method starts at step 202 with the acquisition of pre-procedural images. A 3D model is generated at step 204, and the images and/or 3D model are analyzed to determine the locations of target tissue at step 206. Once the location of target tissue is determined a navigational path through the anatomy of the patient is determined at step 208. With the navigational path through the anatomy is determined the 3D model is registered to the patient's anatomy at step 210. As noted above, this registration may occur some hours, days, or weeks after the acquisition of the pre-procedural images and with the patient in a very different position or location than when they were imaged. Following registration, a catheter or tool is navigated within the patient to the target tissue and the position of a distal portion of the tool or catheter is displayed in the 3D model at step 212. Once proximate the target tissue, in an initial effort to eliminate CT-to-body divergence a local registration is undertaken at step 214. This local registration may include acquisition of fluoroscopic images, detection of the catheter or tool in one or more of the fluoroscopic images, detection of the target tissue in one or more of the fluoroscopic images, and determination of an offset (e.g., distance and direction of the target tissue to the catheter or tool). This offset is then employed to update the displayed relative position of the target tissue and the catheter or tool in the 3D model. This local registration improves the confidence of the clinician in performing the last mile navigation to place the catheter or tool in the target tissue for subsequent diagnostic or therapy procedures. To further improve the clinician's confidence, the respiration rate of the patent can be detected using the reference sensors 118. As described herein above, the reference sensors 118 are EM sensors that are attached to the chest of a patient and in the EM field generated by the transmitter mat 120. The EM fields generated by the transmitter mat 120, which may have a number of antennae, for example 3 or 9 as employed in the ILLUMISITE system or another whole number integer from 1 to 50 antennae, are individually detected by the reference sensors 118. By comparing the detected signals from antennae of the transmitter mat 120 the position and orientation of each reference sensor 118 in the EM field is determined. By monitoring the change in position of each reference sensor over time the respiration rate of the patient can be detected at step 216. This respiration rate information can be transformed into a respiration wave form and displayed in a UI on the computer 122 at step 218. With the display of the respiration waveform, the clinician is able to time the last mile navigation or the insertion of a biopsy or therapy tool to a desired portion of the respiration cycle. And the biopsy or therapy may be performed at step 220 at the desired portion of the respiration waveform.

Figure 3:
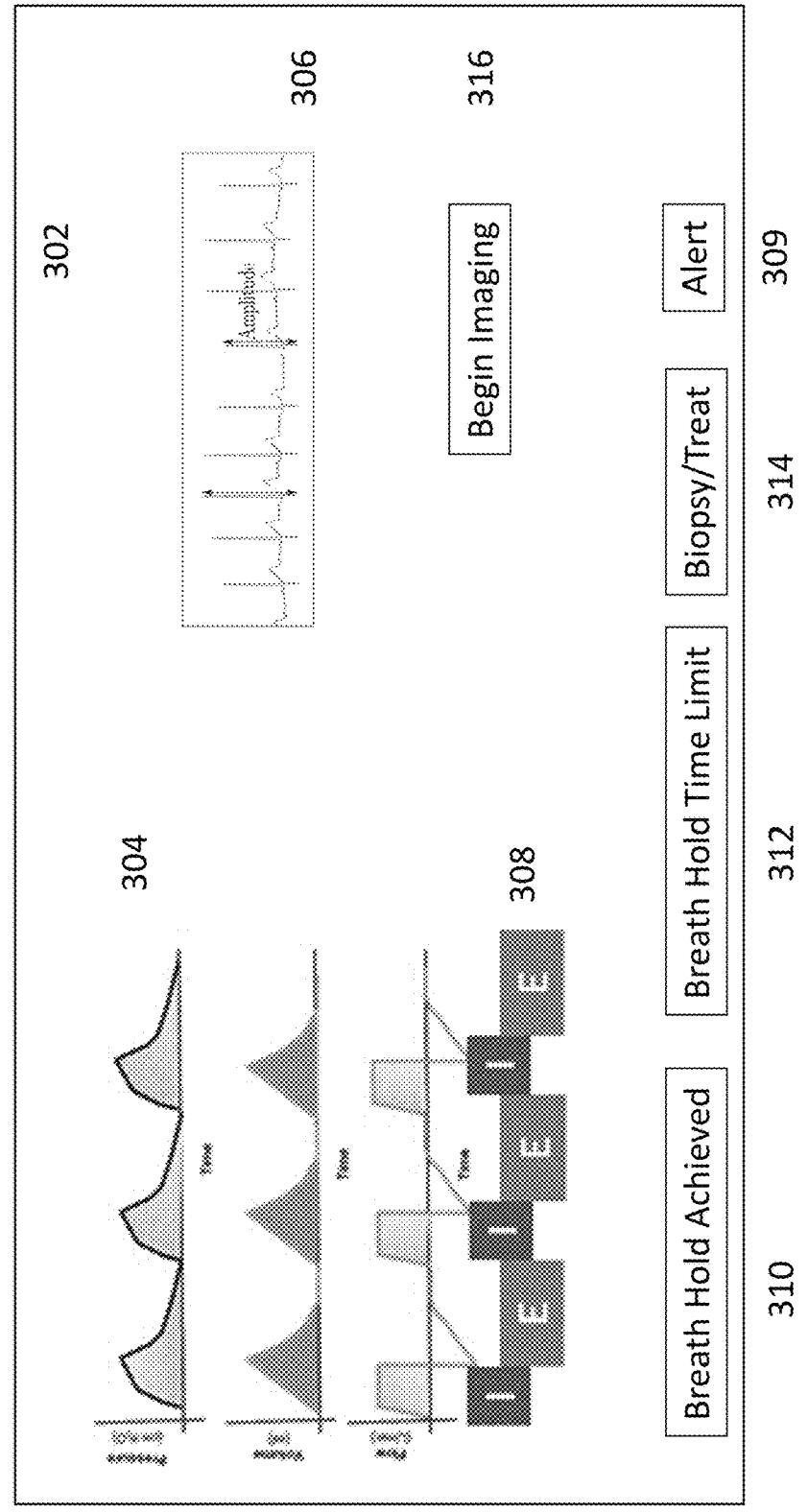
FIG. 3 is a user interface in accordance with the disclosure.

FIG. 3 depicts a UI 302 for presentation on a display associated with computer 122. The UI 302 includes a display of a respiration waveform 304, and a heartrate wave form 306. Those of skill in the art will recognize that the heartrate wave form 306 will be different from a standard echocardiogram (ECG) but atrial and ventricular beats may nonetheless be tracked by the sensors 118, 104, 126 and displayed. The UI 302 may optionally include an indicator 308 depicting the portions of the respiration waveform correlated to the inhalation and the exhalation portions of the respiratory cycle.

In some instances, not just the reference sensors 118 but also the sensors 104 or 126, and their movement within the patient are monitored to detect the heartrate waveform 306 and the respiration waveform 304. In this example the respiration waveform is presented in three forms. First, pressure changes-over-time, second volume changes-over-time, and third flow changes-over-time may each individually or in any desired combination be depicted as separate plots on the UI 302. Finally, the respiration waveform also includes an inhalation/exhalation indicator 308. In addition to displaying the respiration waveform 304, the UI 302 may include an alert 309 that can be highlighted or displayed on the UI 302 to alert the clinician to the occurrence a large change in any of the respiration waveform amplitudes. For example, an unexpectedly large amplitude, indicating a deep breath or significant inhalation may indicate an error in ventilation settings and thus potentially a large change in position of the target tissue. Alternatively, a change in the inspiration/expiration ratio may also trigger a display of the alert 309 to indicate that there may be an error in the ventilation of the patient.

As noted above, the patient for a lung navigation procedure, like many other surgical procedures, is intubated to enable insertion of the bronchoscope 108. The intubation tube enables connection of a ventilator to the intubation tube. A ventilator is essentially a mechanical lung system which ensures that the patient, having been anesthetized, continues necessary and consistent breathing. Ventilation is the primary means in which anesthesia induced atelectasis (partial or full collapse of a lung) is avoided. Ventilators have both an inspiration phase where air is forced into the lungs and an expiration phase where air is drawn from the lungs.

When undertaking a local registration process, as described herein using the fluoroscope 124, it is often desirable to engage in a breath hold procedure. During the breath hold, the ventilator stops forcing air into the patient's lungs (e.g., forced inhalation). In accordance with one aspect of the disclosure, the initiation of a breath hold may be undertaken in coordination with the respiratory wave form. As will be appreciated, the lungs of a patient are an elastic tissue that has tremendous ability to expand. During ventilation, as air is forced into the patient's lungs, the lungs will continue to expand beyond the end of the ventilator's inspiration phase. That is the in-rush of air, under pressure will force the lungs to expand until equilibrium is achieved, and this expansion will continue for some time following the end of the ventilator's inspiration phase until this equilibrium is achieved.

Accordingly, one aspect of the disclosure is directed to optimizing and adjusting the respiration waveform 304 using the inspiration/expiration functions of the ventilator. As such, the ventilator, which may include for example a foot pedal, can be triggered to hold the patient at a determined respiratory position (i.e., desired amount of inflation of the lungs). This may require the ventilator, working in combination with an application running on the computer 122 analyzing the respiratory waveform 304, to determine a time to cease either inspiration or expiration phases of the ventilator to achieve a desired respiratory position of the lungs. That is, using the respiration waveform 304, a time delay or time offset between cessation of ventilator inspiration or expiration and a desired respiration position (e.g., a level of lung inflation) can be determined. This time offset, may be accompanied by an indicator 310 that can be displayed on the UI 302. The indicator may also incorporate an audible signal such as announcing the word "hold" or another term to indicate that breath hold should or is being initiated. This may be particularly useful where the operator of the ventilator is not positioned to see the UI 302. As will be appreciated, this time offset will vary from patient to patient, with a large male patient both requiring greater volumes of air and likely having a greater time offset as compared to a small female patient.

In another aspect of the disclosure an application running on the computer 122 may correlate the respiration waveform 304 collected from the movement of the reference sensors 118 and a ventilator inspiration/expiration wave form. These two waveforms may be analyzed to determine the optimum level of atelectasis that achieves the necessary air flow into the patient, for example to achieve and maintain a desired blood oxygenation level, while at the same time resulting in a relatively small amount of tissue movement from the ventilation. This may also enable a determination of whether the ventilator is optimally set to reduce undesired atelectasis, and in some instances indicate to the nurse or clinician changes in the ventilation protocol are needed to avoid atelectasis.

Another indicator 312 can illuminate on the UI 302 when it is determined that the breath hold has proceeded for too long of a duration. The data for this indicator may be collected from the reference sensors 118 which during the breath hold have not moved other than as a result of the heartbeat, as shown in the heartbeat waveform data 306. Thus, the alert of the breath hold being too long can be completely independent of the actions of the ventilator and based on the lack of movement of the reference sensors 118 on the exterior of the patient. The alert 312 may be passive providing information to the clinician or may be tied to the ventilator to automatically restore normal operation to reduce stress experienced by the patient, who may have a variety of co-morbidities making return to, for example, tidal volume breathing important to the patient.

Figure 4:
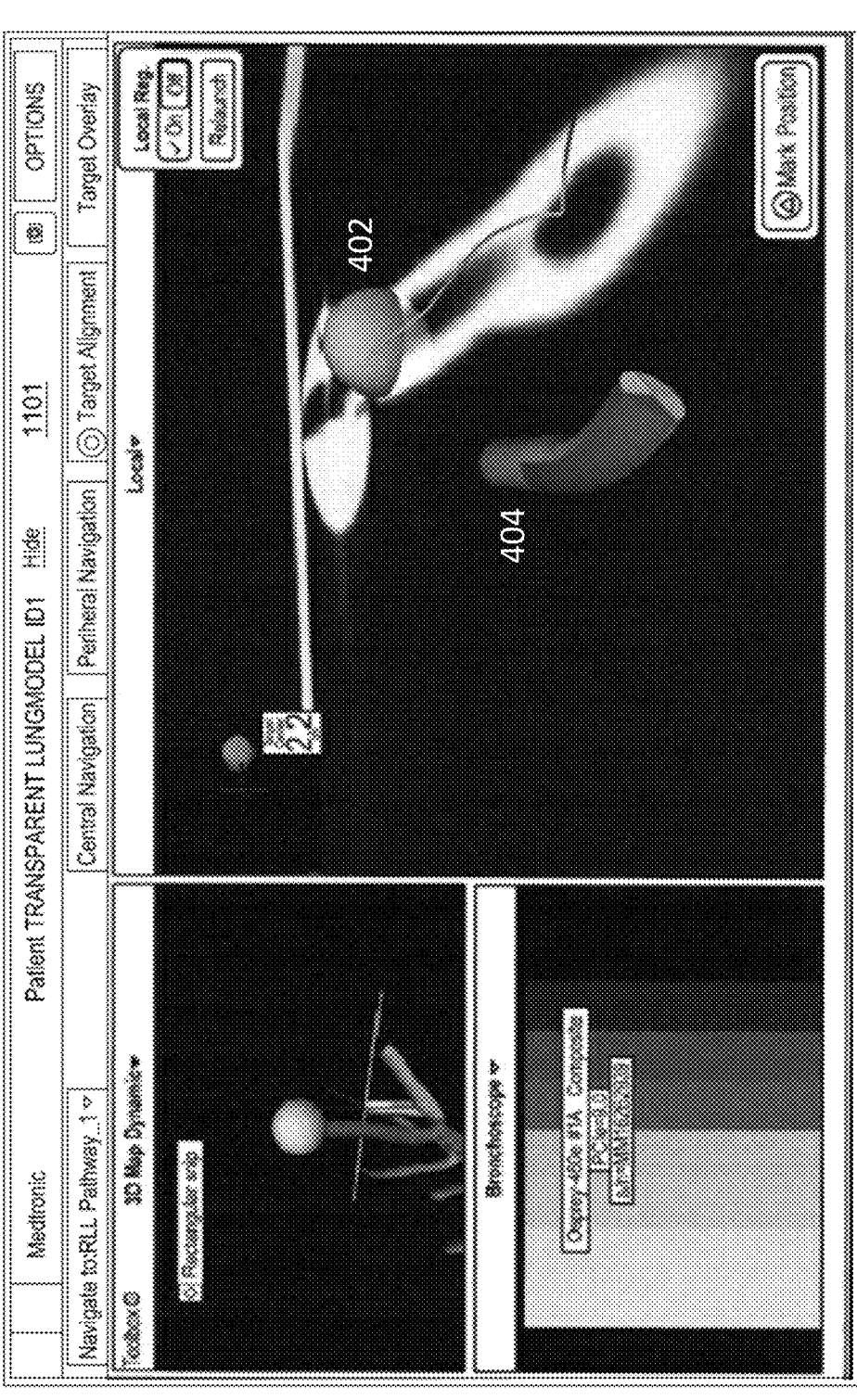
FIG. 4 is a navigation user interface in accordance with the disclosure.

Yet a further indicator 314 that may appear on the UI 302 is a biopsy/treat indicator. This indicator may take a number of forms. As shown in FIG. 3, the biopsy/treat indicator 314 may become illuminated or flash at points in the respiration waveform 304 where the reference sensors 118 are within an acceptable range from the positions they were in during the local registration of step 214. Still further the indicator 314 may transition from a red color to a green color (or other changes in color) to identify the proper times for performing the biopsy or treatment. For example, it is generally understood that inspiration is relatively shorter in duration and the lungs experience a greater rate of change of position during inspiration than during expiration, Thus, the indicator may for example be triggered upon detection of the cessation of the inspiratory phase and become illuminated indicating to the clinician, that the target tissue should be approximately in the same position as during the imaging for the local registration, and will not be experiencing any sudden changes through the majority of the expiration phase of the respiration. As an alternative to the UI 302, in FIG. 4 a UI 400 which depicts a navigational UI of ILLUMISITE and includes a target 402 in its position relative to the catheter or tool 404 following local registration. The target 402 may change color, for example to green during times where capture of a biopsy or placement of a therapy tool is recommended (e.g., coincides with and expiratory phase of the respiration) and may turn red shortly before or as the inspiratory phase of respiration is about to begin. The green target 402 signals the appropriate times for the last mile navigation and the red target 402 signals the times when movement caused by respiration may result in excess movement of the target tissue and may thus result in improper placement of the diagnostic or therapeutic tool during that last mile of navigation.

Still a further aspect of the disclosure is related to an image now indicator 316 depicted on UI 302. The image now indicator 316 can be employed to alert the clinician or an appropriate or optimal time along the respiration waveform 304 for performing imaging using for example the fluoroscope 124. This may be correlated to the breath hold achieved indicator 310 indicating that the movement of the lungs have achieved a state of stability providing high quality imaging. Further, in connection with aspect of the disclosure described in greater detail below, the image now indicator 316 may be employed to trigger imaging during successive or at least multiple respiration cycles. For example, it may be desirable to image during multiple expiration portions of the waveform 304. As noted elsewhere herein, the expiration waveform is substantially more stable and results in a slower rate of movement of the reference sensors 118. Thus, by imaging over multiple expiration phases, a fluoroscopic sweep may be achieved in pieces (e.g., 5-10 degrees per expiration phase) and assembled to achieve a complete fluoroscopic sweep where the lungs are in substantially the same position without requiring a breath hold, and at positions in the respiration waveform that can be again achieved during a treatment/ biopsy phase of the procedure and at which point the biopsy/treat indicator 314 can be illuminated.

Though described herein above with all of the indicators, including the respiration waveform 304 being displayed on the UI 300, not all of these indicators need be displayed on the UI 300. For example, in some instances the UI 200 may only include the biopsy/treat indicator 314 and the image now indicators 316. While the illumination of the biopsy/ treat indicator 314 follows the respiration waveform 304, the waveform itself need not necessarily be displayed in applications of this disclosure. Instead, the illumination of the biopsy/treat indicator 314 would be understood by clinicians that the respiratory state, when illuminated, is stead with minimal change and biopsy or treatment is recommended. A similar analysis and mechanism in presentation on the UI 302 for the image now indicator 316. Thus, the various indicators of the UI 302 described herein above may be used in any combination without departing from the scope of the disclosure.

In connection with the above, data from the ventilator such as the waveforms of the expiration and inspiration phases of mechanical ventilation can be collected by an application on the computing device 122. As noted above, this data can be used to calculate the time offset of the expiration/inspiration waveform and the respiratory waveform generated from the reference sensors 118. This combination of data may further enable the construction of a respiration compensation algorithm. That is, by tracking the movement of the reference sensors 118, either alone or in combination with the sensor 104, as the ventilator moves through its inspiration and expirations cycles. A determination can be made regarding the amount of movement experienced by the tissue proximate the sensor 104 at different times through the respiration waveform. This data enables a compensation algorithm to be developed that automatically updates the relative positions of the target 402 and the catheter 404 as shown in the UI 400. Additionally, a detected sensor position can be amended to that shown in the fluoroscopic images such that any deviation between images in the chest volume from approximately the same location and angle may be compensated for. This may at times be necessary because each scan may not occur optimally at the same point in the respiratory cycle.

In accordance with a further aspect of the disclosure, an algorithm may identify periods during respiration where the sensor 104 is substantially stable and does not move or moves only within a predetermined range over a period of time (e.g., less than 1 mm in 1 second over 3 or more seconds). This data can be coordinated with the UI 400 for the illumination of the target 402 in green for the period of time where there is little to no movement of the sensor 104. This may also be tied to the portions of the respiratory cycle during which the imaging was acquired as described above.

As an alternative to the capturing of the pre-procedure images (e.g., CT scan) at full breath hold, at maximum inflation of the lungs, it may be desirable to capture the pre-procedure images during the expiratory phase of breathing. As is known the normal inspiratory to expiratory ratio (FE ratio) is between 2 and 2.5. This means that a patient is in the expiration phase for about twice as long as the inspiratory phase. Accordingly, the reference sensors 118 can be used to detect a timing of the expiration phase where there is either little movement or movement within a desired range (e.g., less than 1 cm/sec). This timing of the respiration can then be monitored, and the CT scan captured at the detected timing of the expiration phase of the patient while the patient is undergoing an expiratory breath hold. In this manner, the 3D model and other pre-procedure images more closely match the state the lungs are in during a procedure while connected to a ventilator, thus reducing the CT-to-body divergence. Further, the position of the reference sensors at the desired point in the expiration phase can be employed to try to match the position of the patient's chest from the pre-procedure imaging to the lung navigation procedure. Again, an indicator on the UI 300, 400 may help guide the clinician in the appropriate timing for last mile navigation and insertion of a diagnostic or therapy tool into the target tissue. Though described here in the context of the expiration phase of breathing, the same may also be accomplished on the inspiration phase of breathing without departing from the scope of the disclosure.

Still a further aspect of the disclosure is directed to the local registration process described herein above employing the fluoroscope 124. As noted above, following navigation to within about 3 cm of the target tissue, ILLUMISITE provides an opportunity to perform a local registration to update the relative positions of the catheter 404 and target 402, as displayed in the UI 400 of FIG. 4. As noted above, to achieve this local registration a fluoroscopic sweep of the patient is undertaken, with the target tissue and the catheter in the images. In one example, to produce even greater fidelity in the images, as the fluoroscope 124 is rotated about the patient and images are captured, an application running on the computing device 122 is employed to identify those captured images where the reference sensor 118 are at a desired respiration level (e.g., desired point on the respiratory waveform 304). The application, analyzing the images can then identify those images captured outside of the desired respiration level and the angles at which those images are captured. The application can then either automatically drive the fluoroscope 124 to those angles of orientation and capture additional images at the desired respiration level or, the fluoroscope can be manually moved to an indicated angle and imaging can be manually or automatically initiated when the patient's respiration returns to the desired portion of the respiration waveform. As an example, the UI 300 utilizing the for example the indicator 316 may indicate to the clinician the times during the respiration wave form 304 at which images should be captured using the fluoroscope 124 and imaging should be begun. Alternatively or additionally, the indicator 316 may also be used to alert the clinician that automatic imaging is about to commence so that the clinician can avoid being present in the captured images. Once sufficient images have been captured to complete the fluoroscopic sweep, with all images being acquired at the desired respiration level (portion of the respiration waveform), the images may be combined to generate a 3D volumetric reconstruction about the catheter 106 and the target to perform the local registration. As will be appreciated, and described above, the portion of the respiration waveform in which the fluoroscopic images are acquired may also be employed as the period during the respiration waveform at which the indicator 314 to undertake the biopsy or therapy. This helps eliminate any divergence between the position and orientation of the catheter 106 and target in the fluoroscopic sweep that might be caused by respiration.

A further aspect of the disclosure is directed to the registration process. During the registration step data from the sensor 104 is captured and that data may be matched to the 3D model. This enables the navigation of the catheter 106 and sensor 104 and to accurately display the position of the catheter 106 and sensor 104 in the 3D model while being navigated through the airways of the patient. In accordance with the disclosure, the position samples are only acquired either during the expiration phase of breathing, or at certain bands of the respiration waveform 304. By eliminating certain portions of the data acquired by the sensor 104, the registration should be much more accurate.

Still a further aspect of the disclosure is directed to control method for the ventilator based on the respiration waveform 304 from the data collected by the reference sensors 118. In accordance with this aspect of the disclosure for each individual patient, respiration waveform 304 is generated from the reference sensors 118. As will be appreciated by using three separate reference sensors 118 either alone or in combination with data from sensor 104 or 126 different waveforms can be collected for different portions of the lungs. As is known the central airways move very little during respiration, however, the periphery, and particularly the lower portions of the lungs will move significantly during respiration. Accordingly, placement of the reference sensors 118 proximate the position of the lower lobes can provide a guide on relative movement of that portion of the lungs. And placement on or about the sternum can be associated with the expected movement of the trachea or main carina. One or more of the reference sensors 118 may be placed at a location the clinician believes is near the location of the target tissue and thus provide a reasonably accurate measurement of the movement expected by the target tissue through the respiration cycle. From this respiration waveform data in combination with change in position data from the reference sensors 118 enables the formation of a respiration movement model for the individual patient. This individualized lung movement model or algorithm may then be transposed over the entirety of the 3D model of the lung based on the proximity of the target tissue to the central airways, estimated elasticity of the tissue around the target tissue, and the proximity of the target tissue to the position of the reference sensor 118, and other factors known to those of skill in the art. This algorithm can be used to animate the 3D model to depict movement of the target tissue through the respiratory cycle. This animation may be further updated by the addition of movement data from the sensor 104 during a navigation procedure. The personalize respiration model can also be used to inform the ventilator to provide a customized ventilation protocol to achieve both the desired respiration and to minimize movement or at least enable predictable movement of the lungs and the target tissue.

As will be appreciated, through the collection of a large volumes of data and correlating to either patient lung volume or another lung function test, a lung movement estimation can be derived from hundreds or thousands of patients so that a fully personalized model is not required. The same is true of the ventilation protocol, such that the computing device 122 can include an ILLUMISITE ventilation protocol that is signaled to the ventilator to ensure proper ventilation without unnecessary or unplanned movement of airways and the target tissue.

As regards ventilation, in accordance with the disclosure JET ventilation may be employed where high-pressure oxygen rich air is injected into the lungs and allowed to be naturally expired from the lungs. As this oxygen rich air has a higher level of oxygen than ambient air a lower tidal volume can be employed, thus reducing the amount of movement of the lungs during ventilation.

While much of the preceding has been directed to methods of determining movement of the lungs and particularly the target tissue, the disclosure is not so limited. While movement of the lungs must necessarily be managed, a separate factor that must be accounted for is atelectasis. Atelectasis is the collapse of a lung or airway segment. Atelectasis limits the ability of the clinician to navigate the catheter 106 through the patient's airways. The result is that to navigate to a desired location within the lungs, additional force in order to navigate a collapsed segment may result in manual movement of the entire lung or lobe of the lung, and manually changing the shape of the lungs so that they no longer adequately resemble the 3D model being used for the procedure and therefore no longer provide a good guide for navigation. Often once atelectasis is experienced within a portion of the lungs of the patient it is very difficult to reestablish proper inflation in that segment during the procedure.

A starting point for understanding atelectasis for both a particular patient and the population generally is a pulmonary function test (PFT). In a PFT the patient breathes into a device that is configured to measure a number of factors including:

Tidal volume (VT)—the amount of air inhaled or exhaled during normal breathing;

Minute volume (MV)—the total amount of air exhaled per minute;

Vital capacity (VC)—the total volume of air that can be exhaled after inhaling as much as you can;

Functional residual capacity (FRC)—the amount of air left in lungs after exhaling normally;

Residual volume—the amount of air left in the lungs after exhaling as much as the patient can;

Total lung capacity—the total volume of the lungs when filled with as much air as possible;

Forced vital capacity (FVC)—the amount of air exhaled forcefully and quickly after inhaling as much as the patient can;

Forced expiratory volume (FEV)—the amount of air expired during the first, second, and third seconds of the FVC test;

Forced expiratory flow (FEF)—the average rate of flow during the middle half of the FVC test; and Peak expiratory flow rate (PEFR)—the fastest rate that you can force air out of your lungs.

These factors can be analyzed to provide an indication of the elasticity and compliance of the lungs. With elasticity and compliance data a determination can, be made as to the ideal pressure needed in the lungs to maintain the lungs at a stead state (e.g., not experiencing atelectasis). Based on the data from the PFT, an estimation of elasticity and compliance, and the I/E ratio, a minimum acceptable pressure of the lungs may be estimated. That minimum pressure data then can be utilized by the ventilator to ensure that the pressure of the lungs do not drop below that minimum pressure during the procedure. An example, this minimum pressure can be used in conjunction with positive end-expiratory pressure (PEEP) settings of the ventilator to ensure that passive emptying of the lungs does not allow the pressure in the lungs to drop below atmospheric pressure. This is achieved by applying positive pressure to the lungs triggered towards an end of expiration to maintain at least that minimum pressure (e.g., above atmospheric pressure). Those of skill in the art will recognize that these data points may be collected over a large population to develop more generalized protocols that can be used more generally without necessarily requiring a PFT for each individual patient, or to correlate the individual results with the broader data set. Generally, these factors described herein above can be employed to correlate the pressure readings from the PFT with the pressure readings and sensed data from the ventilator to predict the onset of atelectasis of a given segment of the lungs before it happens.

Additionally or alternatively, other patient data that is typically tracked by an anesthesiologist may also inform the clinician and the breathing models described above. As a result, data such as venous pressure and other factors that are the results of for example, a hemodynamic test to provide indicator of the capabilities of the heart and the circulation system of the patient. These heart function factors are typically monitored by the anesthesiologist during a procedure and there is a desired heart function for the procedure that informs the anesthesiologist that the patient is handling the anesthesia well. As will be appreciated, there is overlap between heart function and lung function, thus by tracking both heart function and lung function, including maintaining the minimum pressure the clinician can be confident that atelectasis is being systemically avoided.

While systemic atelectasis avoidance is desired, local measurement and avoidance techniques are also desired. With the data regarding the lung function and/or heart function of the patient including a minimum pressure having been determined, the navigation procedure may commence. As noted above, the catheter 106 is navigated through the patient's airways. Where a bronchoscope 108 is employed during the navigation phase, at some point during the navigation the bronchoscope 108 the bronchoscope 108 becomes wedged in the airways (the scope is larger in diameter than the airway) and the catheter 106 is then navigated further within the airway to the target tissue. The sensor 104, described above as among other things an EM sensor, may in fact be a suite of sensors including the EM sensor, an ultrasound sensor, pressure sensor and others. Indeed, the ultrasound sensor may be a multi-purpose sensor that can be used for imaging, pressure sensing, and palpitation of tissue. As a result, the sensor 104 can be used to monitor airflow from the lung segment being navigated. As the velocity of the airflow from a given airway segment increases and the volume decreases, a determination can be made that the bronchoscope 108 has been wedged. Further, based on the sensed airflow parameters, the quality of the wedging can be assessed.

Relatedly, both the bronchoscope 108 and the catheter 106 may include a working channel. That working channel can be connected separately to the ventilator, or to an alternative inflation source. The working channel of the bronchoscope 108 or catheter 106 can then be employed to ensure that the segment extending beyond the position of the wedged bronchoscope 108 is inflated to at least a desired minimum pressure. This inflation ensures that the airway segment is sufficiently open to allow for additional navigation of the catheter 106 and subsequently diagnostic or therapy tools to the target tissue. In some instances, this process can be employed to reverse local atelectasis of an airway segment. As the local pressure readings are acquired of the lung segment, an indicator may be displayed on the UI 300 or 400 related to the stability of the lung segment for additional navigation of the catheter 106 or tools. Alternatively, an LED or other indicator may be employed on the bronchoscope 108 or catheter 106 to illuminate a portion of the lung segment to inform the clinician that the lung segment is stable and sufficiently inflated or not experiencing atelectasis such that further navigation can be undertaken.

In a related aspect the catheter 106 may include a balloon which in an uninflated state has substantially the same diameter as the catheter 106 and can be inflated to match the diameter of the airway segment in which it is located and inflated. Thus, following wedging of the bronchoscope 108 or catheter 106 the balloon can be inflated. The inflation of the balloon ensures that the airways beyond the balloon are isolated from the remainder of the lungs and essentially perfects the wedging of the scope. As with the methods described above, the isolated segment of the lungs may then be inflated to a desired pressure and a diagnostic or therapeutic tool may then be navigated to the target tissue.

A further aspect of the local inflation of a lung segment relates to the use of a different fluid. Typically ventilators employ an gas mixture that may have additional oxygen added to ensure that the blood of the patient remains property oxygenated, even if the lungs are only being ventilated at tidal volume. However, in accordance with this aspect of the disclosure, the local inflation described above via the working channel of the catheter 106 may be done using a liquid such as saline. Saline will be accepted by the lungs as an inflation medium and so long as it is subsequently suctioned from the lungs will result in no adverse effects to the patient. The saline can apply pressure on the airway walls and allow for an inflation that enables easier navigation. The volume of saline to be employed to inflate the lungs may be determined based on the PFT test or even from the 3D model generated from the pre-procedural images.

Additionally or alternatively, particularly following navigation of a therapeutic tool such as a microwave ablation catheter or an RF ablation catheter to the target tissue, the balloon can be further inflated to reduce the blood flow to the area of the target tissue. Still further, the same working channel that had been used to ensure inflation of the lung segment to a desired pressure for navigation, can then be used to evacuate air from the lung segment. The removal of the air from the lung segment allows the airway to collapse on the therapy catheter. This removal ensures close contact with the therapy catheter and improves the formation of the ablations formed by the therapy catheter by ensuring a consistent dielectric value (i.e., just tissue not any air) around the therapy catheter. Further, by application of pressure on the blood vessels that run along but outside of the airways, blood flow to the target tissue is also reduced. As is known blood flow is a significant heat sink during a therapy procedure. Thus, the combination of evacuation of the airway and use of the balloon to reduce blood flow improves the outcomes of the therapy procedure.

Still a further, aspect of the disclosure is related to the use of dual tube intubation tube. A dual tube intubation tube allows for each lung to be separately ventilated. This allows for one lung to be partially or fully collapsed or at least at a different level of inflation from the other lung. As with the methods and systems described above, the partial or full collapse of the lung, particularly after navigation of a therapeutic catheter to target tissue to enable better and more consistent ablations at the target tissue.

Additionally, a dual tube intubation tube allows for one lung to be normally ventilated and utilized to maintain proper blood oxygenation levels and reduce impact on the patient during the procedure, while the other lung can be isolated and held at a desired pressure or volume of inflation. For example, with the entire or substantially all of the respiratory load being borne by one lung, the other lung may be deflated to a desired pressure that prevents atelectasis and allows for navigation and renders the lung segments in that lung substantially stable such that they do not significantly move as a function of respiration. In such an environment, following a local registration process (e.g., step 214 of method 200) the clinician can be confident of the relative position and orientation of the target tissue and the end of the catheter 106 such that further navigation for placement in the target tissue is reasonably ensured.

Figure 2:
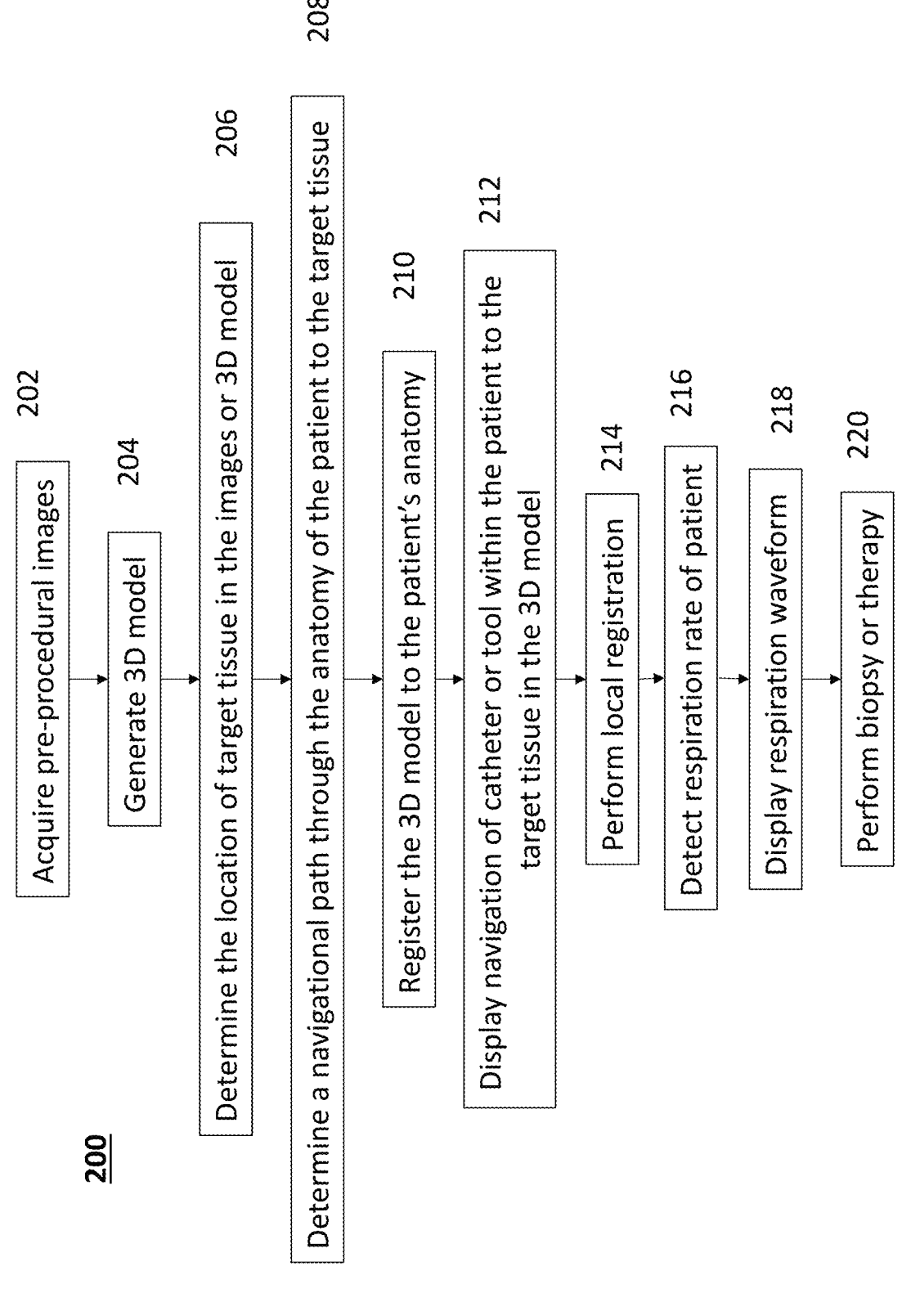
FIG. 2 is a flow diagram depicting a method in accordance with the disclosure.
Figure 5:
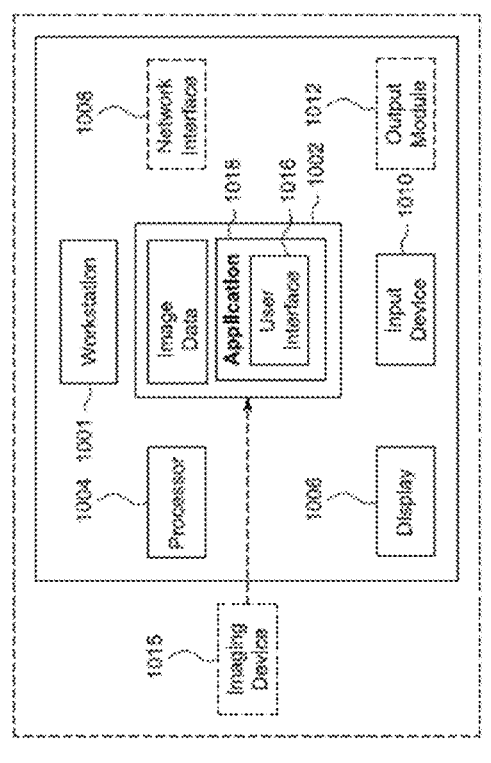
FIG. 5 is a schematic diagram of a computer system in accordance with the disclosure.

Reference is now made to FIG. 5, which is a schematic diagram of a system 1000 configured for use with the methods of the disclosure including the methods of FIG. 2. System 1000 may include a workstation 1001, and optionally connected to fluoroscopic imaging device 124 (FIG. 1). In some aspects, workstation 1001 may be coupled with fluoroscope 1015, directly or indirectly, e.g., by wireless communication. Workstation 1001 may include a memory 1002, a processor 1004, a display 1006 and an input device 1010. Processor 1004 may include one or more hardware processors. Workstation 1001 may optionally include an output module 1012 and a network interface 1008. Memory 1002 may store an application 1018 and image data 1014. Application 1018 may include instructions executable by processor 1004 for executing the methods of the disclosure including the methods of FIG. 2.

Application 1018 may further include a user interface 1016. Image data 1014 may include the CT scans, first and second fluoroscopic images, the generated first and second fluoroscopic 3D reconstructions and/or any other fluoroscopic image data and/or the generated one or more virtual fluoroscopy images. Processor 1004 may be coupled with memory 1002, display 1006, input device 1010, output module 1012, network interface 1008 and fluoroscope 1015. Workstation 1001 may be a stationary computing device, such as a personal computer, or a portable computing device such as a tablet computer. Workstation 1001 may embed multiple computer devices.

Memory 1002 may include any non-transitory computer-readable storage media for storing data and/or software including instructions that are executable by processor 1004 and which control the operation of workstation 1001 and, in some aspects, may also control the operation of fluoroscope 1015. Fluoroscopic imaging device 124 may be used to capture a sequence of fluoroscopic images based on which the fluoroscopic 3D reconstruction is generated and to capture a live 2D fluoroscopic view according to this disclosure. In an aspect, memory 1002 may include one or more storage devices such as solid-state storage devices, e.g., flash memory chips. Alternatively, or in addition to the one or more solid-state storage devices, memory 1002 may include one or more mass storage devices connected to the processor 1004 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 1004. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 1001.

Application 1018 may, when executed by processor 1004, cause display 1006 to present user interface 1016. User interface 1016 may be configured to present to the user a single screen including a three-dimensional (3D) rendering of the tool, the lesion, and/or the catheter of this disclosure. User interface 1016 may be further configured to display the lesion in different colors depending on whether the tool tip is aligned with the lesion in three dimensions.

Network interface 1008 may be configured to connect to a network such as a local area network (LAN) consisting of a wired network and/or a wireless network, a wide area network (WAN), a wireless mobile network, a Bluetooth network, and/or the Internet. Network interface 1008 may be used to connect between workstation 1001 and fluoroscope 1015. Network interface 1008 may be also used to receive image data 1014. Input device 1010 may be any device by which a user may interact with workstation 1001, such as, for example, a mouse, keyboard, foot pedal, touch screen, and/or voice interface. Output module 1012 may include any connectivity port or bus, such as, for example, parallel ports, serial ports, universal serial busses (USB), or any other similar connectivity port known to those skilled in the art.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects.

What is claimed is:

1. A method of respiration compensation comprising:

detecting a position of a catheter proximate a target within a patient;

performing a local registration to update a displayed relative position and orientation of the catheter and the target in a three-dimensional model;

detecting movement of a plurality of sensors;

determining a respiration waveform from the detected movement of the plurality of sensors;

receiving a ventilation waveform from a ventilator operably connected to the patient to undertake respiration wherein the ventilation waveform is configured to achieve a desired respiration waveform;

detecting achievement of a breath hold of the patient wherein breath hold is achieved following cessation of ventilation of the patient and an off-set period to allow for expansion of lungs of the patient wherein the off-set period is calculated based on comparison of the ventilation waveform and the respiration waveform; and indicating on a user-interface a period during which advancement of a biopsy or therapy tool from the catheter is most likely to intersect the target, wherein the period corresponds to a portion of the respiration waveform during which the movement of the plurality of sensors is within a desired range.

2. The method of claim 1, wherein the period is during an expiration phase of the respiration waveform.

3. The method of claim 1, further comprising displaying the respiration waveform on the user-interface.

4. The method of claim 1, wherein performing the local registration further comprises receiving fluoroscopic images and identifying those images acquired during a desired portion of the respiration waveform.

5. The method of claim 4, further comprising determining angles at which additional images are required to complete a fluoroscopic sweep.

6. The method of claim 5, further comprising orienting a fluoroscope to the determined angles and collecting the additional images during a desired portion of the respiration waveform to complete the fluoroscopic sweep.

7. The method of claim 6 further comprising, wherein the orienting of the fluoroscope is performed automatically.

8. The method of claim 1, wherein performing the local registration further comprises receiving fluoroscopic images and identifying those images acquired during a desired portion of the respiration waveform.

9. The method of claim 8, further comprising determining angles at which additional images are required to complete a fluoroscopic sweep.

10. The method of claim 9, further comprising orienting a fluoroscope to the determined angles and collecting the additional images during a desired portion of the respiration waveform to complete the fluoroscopic sweep.

11. The method of claim 10 further comprising, wherein the orienting of the fluoroscope is performed automatically.

12. A method of respiration compensation comprising:

detecting movement of a plurality of sensors;

determining a respiration waveform from the detected movement of the plurality of sensors;

detecting a position of a catheter proximate a target within a patient;

determining a respiration waveform from the detected movement of the plurality of sensors;

receiving a ventilation waveform from a ventilator operably connected to the patient to undertake respiration wherein the ventilation waveform is configured to achieve a desired respiration waveform;

detecting achievement of a breath hold of the patient, wherein breath hold is achieved following cessation of ventilation of the patient and an off-set period to allow for expansion of lungs of the patient wherein the off-set period is calculated based on comparison of the ventilation waveform and the respiration waveform;

acquiring a plurality of fluoroscopic images with a fluoroscope, wherein the fluoroscopic images include a distal portion of the catheter and the target;

identifying individual images of the plurality of fluoroscopic images acquired during a desired portion of the respiration waveform;

determining angles at which additional images are required to complete a fluoroscopic sweep;

orienting the fluoroscope to the determined angles and collecting additional images during a desired portion of the respiration waveform to complete the fluoroscopic sweep;

performing a local registration, by identifying the catheter and the target in two or more images from the fluoroscopic sweep;

updating a displayed relative position and orientation of the catheter and the target in a 3D model; and indicating on a user-interface a period during which advancement of a biopsy or therapy tool from the catheter is most likely to intersect the target, wherein the period corresponds to the desired portion of the respiration waveform.

13. The method of claim 12, wherein the desired portion of the respiration waveform is a portion with a slowest rate of change of position of the plurality of sensors.

14. The method of claim 13, wherein the desired portion of the respiration waveform is a part of an expiration phase.

15. The method of claim 12, wherein the ventilation waveform is configured to minimize movement of the plurality of sensors and achieve a desire state of inflation of lungs of the patient.

16. The method of claim 15, further comprising inflating a balloon configured proximate a distal end of the catheter, wherein the balloon is configured to reduce blood and airflow distal of the balloon in the lungs of the patient.

17. A method of respiration compensation comprising:

detecting a position of a catheter proximate a target within a patient;

detecting movement of a plurality of sensors;

determining a respiration waveform from the detected movement of the plurality of sensors;

receiving a ventilation waveform from a ventilator operably connected to the patient to undertake respiration wherein the ventilation waveform is configured to achieve a desired respiration waveform;

detecting achievement of a breath hold of the patient wherein breath hold is achieved following cessation of ventilation of the patient and an off-set period to allow for expansion of lungs of the patient wherein the off-set period is calculated based on comparison of the ventilation waveform and the respiration waveform; and indicating on a user-interface a period during which advancement of a biopsy or therapy tool from the catheter is most likely to intersect a target, wherein the period corresponds to a portion of the respiration waveform during which the movement of the plurality of sensors is within a desired range.

18. The method of claim 17, further comprising performing a local registration to update a displayed relative position and orientation of the catheter and a target in a three-dimensional model.

19. The method of claim 17, wherein the period is during an expiration phase of the respiration waveform.

20. The method of claim 17, further comprising displaying the respiration waveform on the user-interface.

* * * * *